United States Patent
Vardi (10) Patent No.: US 8,771,342 B2
(45) Date of Patent: Jul. 8, 2014

(54) METHODS FOR DEPLOYING STENTS IN BIFURCATIONS

(75) Inventor: Gil Vardi, Town and Country, MO (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 727 days.

(21) Appl. No.: 12/555,501

(22) Filed: Sep. 8, 2009

(65) Prior Publication Data

US 2009/0326634 A1   Dec. 31, 2009

Related U.S. Application Data (63) Continuation of application No. 10/320,719, filed on Dec. 17, 2002, now Pat. No. 7,591,846.

(51) Int. Cl.
*A61F 2/06* (2013.01)

(52) U.S. Cl.
USPC .......................... 623/1.35; 606/198; 606/194

(58) Field of Classification Search
USPC ............ 623/1.11, 1.12, 1.19, 1.25, 1.3, 1.35, 623/1.49, 1.13, 1.14, 1.15, 1.23; 606/191–198, 108
See application file for complete search history.

(56) References Cited

U.S. PATENT DOCUMENTS

| | | |
|---|---|---|
| 1,596,754 A | 8/1926 | Moschelle |
| 3,657,744 A | 4/1972 | Ersek |
| 3,872,893 A | 3/1975 | Roberts |
| 4,140,126 A | 2/1979 | Choudhury |
| 4,309,994 A | 1/1982 | Grunwald |
| 4,385,631 A | 5/1983 | Uthmann |
| 4,410,476 A | 10/1983 | Redding et al. |
| 4,413,989 A | 11/1983 | Schjeldahl et al. |
| 4,421,810 A | 12/1983 | Rasmussen |
| 4,453,545 A | 6/1984 | Inoue |

(Continued)

FOREIGN PATENT DOCUMENTS

| | | |
|---|---|---|
| CA | 2318314 | 7/1999 |
| CA | 2403826 | 9/2001 |

(Continued)

OTHER PUBLICATIONS

Caputo et al., "Stent Jail: A Minimum-Security Prison," The American Journal of Cardiology, vol. 77, pp. 1226-1230, Jun. 1, 1996.

(Continued)

*Primary Examiner* — Darwin Erezo
*Assistant Examiner* — Katrina Stransky
(74) *Attorney, Agent, or Firm* — Seager, Tufte & Wickhem LLC (57) ABSTRACT

A method of deploying a stent in a bifurcation includes introducing two guidewires through the main vessel and using the two guidewires for guiding a dual lumen catheter carrying a stent first to an initial position proximal to the stent deployment position, retracting one wire, and projecting it from the catheter and through a side of the stent a branch guidewire into the second branch vessel, and then moving the catheter to the predetermined deployment position while guided by the main guidewire in the first branch vessel, and the branch guidewire in the second branch vessel. The stent is then expanded, and the catheter is removed with the stent remaining in its deployed position An alternative embodiment includes introducing one wire, advancing the system over the one wire and subsequently introducing the second wire.

17 Claims, 6 Drawing Sheets

(56) References Cited

U.S. PATENT DOCUMENTS

| | | |
|---|---|---|
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Palmaz |
| 4,759,748 A | 7/1988 | Reed |
| 4,762,128 A | 8/1988 | Rosenbluth |
| 4,769,029 A | 9/1988 | Patel |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz et al. |
| 4,946,464 A | 8/1990 | Pevsner |
| 4,957,501 A | 9/1990 | Lahille et al. |
| 4,957,508 A | 9/1990 | Kaneko et al. |
| 4,964,850 A | 10/1990 | Bouton et al. |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,170 A | 10/1991 | Cameron |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang et al. |
| 5,122,125 A | 6/1992 | Deuss |
| 5,135,536 A | 8/1992 | Hillstead |
| 5,147,317 A | 9/1992 | Shank et al. |
| 5,159,920 A | 11/1992 | Condon et al. |
| 5,176,617 A | 1/1993 | Fischell et al. |
| 5,192,297 A | 3/1993 | Hull |
| 5,195,984 A | 3/1993 | Schatz |
| 5,211,683 A | 5/1993 | Maginot |
| 5,217,440 A | 6/1993 | Frassica |
| 5,222,971 A | 6/1993 | Willard et al. |
| 5,226,913 A | 7/1993 | Pinchuk |
| 5,234,457 A | 8/1993 | Andersen |
| 5,236,446 A | 8/1993 | Dumon |
| 5,244,619 A | 9/1993 | Burnham |
| 5,254,619 A | 10/1993 | Ando |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A | 6/1994 | Sahota |
| 5,324,257 A | 6/1994 | Osborne et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,383,892 A | 1/1995 | Cardon et al. |
| 5,387,235 A | 2/1995 | Chuter |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun et al. |
| 5,437,638 A | 8/1995 | Bowman |
| 5,443,497 A | 8/1995 | Venbrux |
| 5,445,624 A | 8/1995 | Jimenez |
| 5,449,373 A | 9/1995 | Pinchasik et al. |
| 5,449,382 A | 9/1995 | Dayton |
| 5,456,694 A | 10/1995 | Marin et al. |
| 5,456,712 A | 10/1995 | Maginot |
| 5,456,714 A | 10/1995 | Owen |
| 5,458,605 A | 10/1995 | Klemm |
| 5,462,530 A | 10/1995 | Jang |
| 5,476,471 A | 12/1995 | Shifrin et al. |
| 5,489,271 A | 2/1996 | Andersen |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau et al. |
| 5,507,769 A | 4/1996 | Marin et al. |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,562,726 A | 10/1996 | Chuter |
| 5,569,295 A | 10/1996 | Lam |
| 5,571,087 A | 11/1996 | Ressemann et al. |
| 5,575,771 A | 11/1996 | Walinsky |
| 5,575,817 A | 11/1996 | Martin |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,605 A | 3/1997 | Marshall et al. |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A | 10/1997 | Marcade |
| 5,676,697 A | 10/1997 | McDonald |
| 5,679,400 A | 10/1997 | Tuch |
| 5,683,451 A | 11/1997 | Lenker et al. |
| 5,690,642 A | 11/1997 | Osborne et al. |
| 5,693,084 A | 12/1997 | Chuter |
| 5,693,086 A | 12/1997 | Goicoechea et al. |
| 5,693,088 A | 12/1997 | Lazarus |
| 5,697,971 A | 12/1997 | Fischell et al. |
| 5,707,354 A | 1/1998 | Salmon et al. |
| 5,709,713 A | 1/1998 | Evans et al. |
| 5,716,365 A | 2/1998 | Goicoechea et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |
| 5,749,825 A | 5/1998 | Fischell et al. |
| 5,749,848 A | 5/1998 | Jang et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |

(56) References Cited

U.S. PATENT DOCUMENTS

| | | |
|---|---|---|
| 5,755,778 A | 5/1998 | Kleshinski |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,536 A | 2/1999 | Lazarus |
| 5,871,537 A | 2/1999 | Holman et al. |
| 5,891,133 A | 4/1999 | Murphy-Chutorian |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,928,248 A | 7/1999 | Acker |
| 5,938,682 A | 8/1999 | Hojebane et al. |
| 5,938,696 A | 8/1999 | Goicoechea et al. |
| 5,948,016 A | 9/1999 | Jang |
| 5,951,599 A | 9/1999 | McCrory |
| 5,961,548 A | 10/1999 | Shmulewitz |
| 5,967,986 A | 10/1999 | Cimochowski et al. |
| 5,972,018 A | 10/1999 | Israel et al. |
| 6,007,517 A | 12/1999 | Anderson |
| 6,013,054 A | 1/2000 | Jiun Yan |
| 6,013,091 A | 1/2000 | Ley et al. |
| 6,017,324 A | 1/2000 | Tu et al. |
| 6,017,363 A | 1/2000 | Hojeibane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | Von Oepen |
| 6,051,020 A * | 4/2000 | Goicoechea et al. .......... 623/1.35 |
| 6,056,775 A | 5/2000 | Borghi et al. |
| 6,059,823 A | 5/2000 | Holman et al. |
| 6,059,824 A | 5/2000 | Taheri |
| 6,066,168 A | 5/2000 | Lau et al. |
| 6,068,655 A | 5/2000 | Seguin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,096,073 A | 8/2000 | Webster et al. |
| 6,099,497 A | 8/2000 | Adams et al. |
| 6,102,938 A | 8/2000 | Evans et al. |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,152,945 A | 11/2000 | Bachinski et al. |
| 6,165,195 A * | 12/2000 | Wilson et al. ................. 606/194 |
| 6,165,197 A | 12/2000 | Yock |
| 6,165,214 A | 12/2000 | Lazarus |
| 6,179,867 B1 | 1/2001 | Cox |
| 6,183,506 B1 | 2/2001 | Penn et al. |
| 6,183,509 B1 | 2/2001 | Dibie |
| 6,190,353 B1 | 2/2001 | Makower et al. |
| 6,190,403 B1 | 2/2001 | Fischell et al. |
| 6,193,746 B1 | 2/2001 | Strecker |
| 6,203,568 B1 | 3/2001 | Lombardi et al. |
| 6,203,569 B1 | 3/2001 | Wijay |
| 6,210,380 B1 | 4/2001 | Mauch |
| 6,210,429 B1 | 4/2001 | Vardi et al. |
| 6,217,527 B1 | 4/2001 | Selmon et al. |
| 6,221,080 B1 | 4/2001 | Power |
| 6,221,090 B1 | 4/2001 | Wilson |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,251,133 B1 | 6/2001 | Richter et al. |
| 6,258,073 B1 | 7/2001 | Mauch |
| 6,258,099 B1 | 7/2001 | Mareiro et al. |
| 6,258,116 B1 | 7/2001 | Hojeibane |
| 6,258,121 B1 | 7/2001 | Yang et al. |
| 6,261,273 B1 | 7/2001 | Ruiz |
| 6,261,305 B1 | 7/2001 | Marotta et al. |
| 6,261,319 B1 | 7/2001 | Kveen et al. |
| 6,264,682 B1 | 7/2001 | Wilson et al. |
| 6,273,911 B1 | 8/2001 | Cox et al. |
| 6,273,913 B1 | 8/2001 | Wright et al. |
| 6,287,314 B1 | 9/2001 | Lee et al. |
| 6,290,673 B1 | 9/2001 | Shanley |
| 6,293,967 B1 | 9/2001 | Shanley |
| 6,299,634 B1 | 10/2001 | Bergeron |
| 6,302,906 B1 | 10/2001 | Goicoechea et al. |
| 6,309,412 B1 | 10/2001 | Lau et al. |
| 6,309,414 B1 | 10/2001 | Rolando et al. |
| 6,312,459 B1 | 11/2001 | Huang et al. |
| 6,325,821 B1 | 12/2001 | Gaschino et al. |
| 6,325,826 B1 | 12/2001 | Vardi et al. |
| 6,334,870 B1 | 1/2002 | Ehr et al. |
| 6,346,089 B1 | 2/2002 | Dibie |
| 6,350,278 B1 | 2/2002 | Lenker et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,371,978 B1 | 4/2002 | Wilson |
| 6,383,213 B2 | 5/2002 | Wilson et al. |
| 6,383,215 B1 | 5/2002 | Sass |
| 6,387,120 B2 | 5/2002 | Wilson et al. |
| 6,395,018 B1 | 5/2002 | Castaneda |
| 6,398,792 B1 | 6/2002 | O'Connor |
| 6,398,804 B1 | 6/2002 | Spielberg |
| 6,428,567 B2 | 8/2002 | Wilson et al. |
| 6,428,570 B1 | 8/2002 | Globerman |
| 6,432,133 B1 | 8/2002 | Lau et al. |
| 6,436,104 B2 | 8/2002 | Hojeibane |
| 6,436,134 B2 | 8/2002 | Richter et al. |
| 6,468,302 B2 | 10/2002 | Cox et al. |
| 6,475,208 B2 | 11/2002 | Mauch |
| 6,478,816 B1 | 11/2002 | Kveen et al. |
| 6,482,211 B1 | 11/2002 | Choi |
| 6,485,511 B2 | 11/2002 | Lau et al. |
| 6,494,905 B1 | 12/2002 | Zedler et al. |
| 6,508,836 B2 | 1/2003 | Wilson et al. |
| 6,511,504 B1 | 1/2003 | Lau et al. |
| 6,511,505 B2 | 1/2003 | Cox et al. |
| 6,520,988 B1 | 2/2003 | Colombo et al. |

(56) References Cited

U.S. PATENT DOCUMENTS

| | | | |
|---|---|---|---|
| 6,527,799 B2 | 3/2003 | Shanley |
| 6,540,719 B2 | 4/2003 | Bigus et al. |
| 6,540,779 B2 | 4/2003 | Richter et al. |
| 6,572,647 B1 | 6/2003 | Supper et al. |
| 6,576,009 B2 | 6/2003 | Ryan et al. |
| 6,579,309 B1 | 6/2003 | Loos et al. |
| 6,579,312 B2 | 6/2003 | Wilson et al. |
| 6,582,394 B1 | 6/2003 | Reiss et al. |
| 6,582,459 B1 | 6/2003 | Lau et al. |
| 6,596,020 B2 | 7/2003 | Vardi et al. |
| 6,596,022 B2 | 7/2003 | Lau et al. |
| 6,599,315 B2 | 7/2003 | Wilson |
| 6,599,316 B2 | 7/2003 | Vardi et al. |
| 6,602,284 B2 | 8/2003 | Cox et al. |
| 6,641,609 B2 | 11/2003 | Globerman |
| 6,645,241 B1 | 11/2003 | Strecker |
| 6,652,573 B2 | 11/2003 | von Oepen |
| 6,669,717 B2 | 12/2003 | Marotta et al. |
| 6,676,667 B2 | 1/2004 | Mareiro et al. |
| 6,679,911 B2 | 1/2004 | Burgermeister |
| 6,682,536 B2 | 1/2004 | Vardi et al. |
| 6,689,156 B1 | 2/2004 | Davidson et al. |
| 6,692,483 B2 | 2/2004 | Vardi et al. |
| 6,695,877 B2 | 2/2004 | Brucker et al. |
| 6,706,062 B2 | 3/2004 | Vardi et al. |
| 6,709,440 B2 | 3/2004 | Callol et al. |
| 6,736,841 B2 | 5/2004 | Musbach et al. |
| 6,770,092 B2 | 8/2004 | Richter |
| 6,780,174 B2 | 8/2004 | Mauch |
| 6,802,856 B2 | 10/2004 | Wilson |
| 6,827,735 B2 | 12/2004 | Greenberg |
| 6,827,736 B2 | 12/2004 | Perouse |
| 6,843,803 B2 | 1/2005 | Ryan et al. |
| 6,852,124 B2 | 2/2005 | Cox et al. |
| 6,855,125 B2 | 2/2005 | Shanley |
| 6,884,258 B2 | 4/2005 | Vardi et al. |
| 6,890,349 B2 | 5/2005 | McGuckin, Jr. et al. |
| 6,896,699 B2 | 5/2005 | Wilson et al. |
| 6,908,477 B2 | 6/2005 | McGuckin, Jr. et al. |
| 6,942,689 B2 | 9/2005 | Majercak |
| 6,955,687 B2 | 10/2005 | Richter et al. |
| 6,955,688 B2 | 10/2005 | Wilson et al. |
| 6,962,602 B2 | 11/2005 | Vardi et al. |
| 6,980,174 B2 | 12/2005 | Flasza et al. |
| 7,056,323 B2 | 6/2006 | Mareiro et al. |
| 7,105,019 B2 | 9/2006 | Hojeibane |
| 7,118,593 B2 | 10/2006 | Davidson et al. |
| 7,125,419 B2 | 10/2006 | Sequin et al. |
| 7,163,553 B2 | 1/2007 | Limon |
| 7,220,275 B2 | 5/2007 | Davidson et al. |
| 7,238,197 B2 | 7/2007 | Sequin et al. |
| 7,244,853 B2 | 7/2007 | Schreiber et al. |
| 7,252,679 B2 | 8/2007 | Fischell et al. |
| 7,344,514 B2 | 3/2008 | Shanley |
| 7,387,639 B2 | 6/2008 | Bourang et al. |
| 7,591,846 B2 | 9/2009 | Vardi |
| 2001/0037146 A1 | 11/2001 | Lau et al. |
| 2001/0039448 A1 | 11/2001 | Dibie |
| 2002/0013618 A1 | 1/2002 | Marotta et al. |
| 2002/0032478 A1 | 3/2002 | Boekstegers et al. |
| 2002/0035392 A1 | 3/2002 | Wilson |
| 2002/0058990 A1 | 5/2002 | Jang |
| 2002/0111675 A1 | 8/2002 | Wilson |
| 2002/0123790 A1 | 9/2002 | White et al. |
| 2002/0156516 A1 | 10/2002 | Vardi et al. |
| 2002/0165604 A1 | 11/2002 | Shanley |
| 2002/0183763 A1 | 12/2002 | Callol et al. |
| 2002/0193872 A1 | 12/2002 | Trout, III et al. |
| 2002/0193873 A1 | 12/2002 | Brucker et al. |
| 2003/0009209 A1 | 1/2003 | Hojelbane |
| 2003/0009214 A1 | 1/2003 | Shanley |
| 2003/0014102 A1 | 1/2003 | Hong et al. |
| 2003/0125802 A1 | 7/2003 | Callol et al. |
| 2004/0015227 A1 | 1/2004 | Vardi et al. |
| 2004/0049259 A1 | 3/2004 | Strecker |
| 2004/0148006 A1 | 7/2004 | Davidson et al. |
| 2005/0075722 A1 | 4/2005 | Chuter |
| 2005/0245941 A1 | 11/2005 | Vardi et al. |
| 2007/0179591 A1 | 8/2007 | Baker et al. |
| 2008/0255581 A1 | 10/2008 | Bourang et al. |

FOREIGN PATENT DOCUMENTS

| | | |
|---|---|---|
| DE | 9014845.2 | 9/1991 |
| DE | 29701758 | 3/1997 |
| DE | 60036233 | 5/2008 |
| EP | 0891751 | 1/1999 |
| EP | 0897700 | 2/1999 |
| EP | 0904745 | 3/1999 |
| EP | 1031328 | 8/2000 |
| EP | 0884028 | 2/2002 |
| EP | 0646365 | 1/2004 |
| EP | 0684022 | 2/2004 |
| EP | 0897698 | 6/2004 |
| EP | 1182989 | 12/2004 |
| EP | EP 0551179 | 4/2005 |
| EP | 1157674 | 7/2005 |
| EP | 0804907 | 11/2005 |
| EP | 1031330 | 11/2005 |
| EP | 0876805 | 8/2006 |
| EP | 1512380 | 8/2007 |
| FR | 2678508 | 1/1993 |
| JP | 8-299456 | 11/1996 |
| WO | WO 88/06026 | 8/1988 |
| WO | WO 90/13332 | 11/1990 |
| WO | WO 91/12779 | 9/1991 |
| WO | WO 92/19308 | 11/1992 |
| WO | WO 95/08965 | 4/1995 |
| WO | WO 95/21592 | 8/1995 |
| WO | WO 96/29955 | 10/1996 |
| WO | WO 96/34580 | 11/1996 |
| WO | WO 96/41592 | 12/1996 |
| WO | WO 97/09946 | 3/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41803 | 11/1997 |
| WO | WO 97/45073 | 12/1997 |
| WO | WO 98/17204 | 4/1998 |
| WO | WO 98/19628 | 5/1998 |
| WO | WO 98/35634 | 8/1998 |
| WO | WO 98/36709 | 8/1998 |
| WO | WO 98/44871 | 10/1998 |
| WO | WO 98/48733 | 11/1998 |
| WO | WO 98/52497 | 11/1998 |
| WO | WO 99/00835 | 1/1999 |
| WO | WO 99/15103 | 4/1999 |
| WO | WO 99/17680 | 4/1999 |
| WO | WO 99/34749 | 7/1999 |
| WO | WO 99/35979 | 7/1999 |
| WO | WO 99/36002 | 7/1999 |
| WO | WO 99/39661 | 8/1999 |
| WO | WO 99/49793 | 10/1999 |
| WO | WO 99/58059 | 11/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/53122 | 9/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/068012 | 9/2002 |
| WO | WO 02/076333 | 10/2002 |
| WO | WO 02/094336 | 11/2002 |
| WO | WO 03/055414 | 7/2003 |
| WO | WO 2004/026180 | 4/2004 |
| WO | WO 2006/124162 | 11/2006 |

(56) References Cited

FOREIGN PATENT DOCUMENTS

OTHER PUBLICATIONS

Carrie et al., ""T"-Shaped Stent Placement: A Technique for the Treatment of Dissected Bifurcation Lesions," Catheterization and Cardiovascular Diagnosis, vol. 37, pp. 311-313, 1996.

Chevalier et al., "Placement of Coronary Stents in Bifurcation Lesions by the "Culotte" Technique," The American Journal of Cardiology, vol. 82, pp. 943-949, Oct. 15, 1998.

Colombo et al., ""Kissing" Stents for Bifurcational Coronary Lesion," Catheterization and Cardiovascular Diagnosis, vol. 30, pp. 327-330, 1993.

U.S. Appl. No. 08/642,297, filed May 3, 1996, to Richter et al.

U.S. Appl. No. 09/325,996, filed Jun. 4, 1999, to Vardi et al.

U.S. Appl. No. 09/533,616, filed Mar. 22, 2000, to Vardi et al.

U.S. Appl. No. 09/614,472, filed Jul. 11, 2000, to Davidson et al.

U.S. Appl. No. 09/663,111, filed Sep. 15, 2000, to Davidson et al.

Dichek et al., "Seeding of Intravascular Stents with Genetically Engineered Endothelial Cells," Circulation, vol. 80, No. 5, pp. 1347-1353, Nov. 1989.

Fischman et al., "A Randomized Comparison of Coronary-Stent Placement and Balloon Angioplasty in the Treatment of Coronary Artery Disease," New England Journal of Medicine, vol. 331, No. 8, pp. 496-501, Aug. 25, 1994.

Katoh et al., "New Double Wire Technique to Stent Ostial Lesions," Catheterization and Cardiovascular Diagnosis, vol. 40, pp. 400-402, 1997.

Lear et al., "The Northridge Earthquake as a Trigger for Acute Myocardial Infarction," 1 page, 1996.

Lewis et al., "Acute Procedural Results in the Treatment of 30 Coronary Artery Bifurcation Lesions with a Double-Wire Atherectomy Technique for Side-Branch Protection," American Heart Journal, vol. 127, No. 6, pp. 1600-1607, 1994.

Nakamura et al., "Techniques for Palmaz-Schatz Stent Deployment in Lesions with a Large Side Branch," Catheterization and Cardiovascular Diagnosis, vol. 34, pp. 353-361, 1995.

Satler et al. "Bifurcation Disease: To Treat or Not to Treat," Catheterization and Cardiovascular Interventions, vol. 50, pp. 411-412, 2000.

SCIMED Life Systems, Inc., "TRIO 14 PTCA Catheter, Re-Engineering Over-The-Wire Balloon Technology," Brochure, 4 pages, 1994.

Serruys et al., "A Comparison of Balloon Expandable-Stent Implantation with Balloon Angioplasty in Patients with Coronary Artery Disease," The New England Journal of Medicine, vol. 331, No. 8, pp. 489-495, Aug. 25, 1994.

Yamashita et al., "Bifurcation Lesions: Two Stents Versus One Stent—Immediate and Follow-up Results," Journal of the American College of Cardiology, vol. 35, No. 5, pp. 1145-1151, Apr. 2000.

\* cited by examiner

METHODS FOR DEPLOYING STENTS IN BIFURCATIONS

This application is a continuation of U.S. patent application Ser. No. 10/320,719, filed Dec. 17, 2002, now issued as U.S. Pat. No. 7,591,846, which application is incorporated herein by reference in its entirety.

FIELD AND BACKGROUND OF THE INVENTION

The present invention relates to the delivery of stents. A stent is a type of endoprosthesis device, typically intraluminally placed or implanted within a vein, artery, or other tubular body organ for treating an occlusion, stenosis, aneurysm, collapse, dissection, or weakened, diseased, or abnormally dilated vessel or vessel wall, by expanding the vessel or by reinforcing the vessel wall. In particular, stents are quite commonly implanted into the coronary, pulmonary, neurovascular, peripheral vascular, renal, gastrointestinal and reproductive systems, in order to reinforce individual body organs. The invention described herein is particularly useful for deploying stents in bifurcations, and is therefore described below with respect to this application.

In vessel bifurcations, a main vessel splits into two branch vessels. Implanting stents in bifurcations is particularly problematic because of the need to precisely locate the stent both longitudinally and radially in the bifurcation. This is especially the case when the stent is designed with a side opening which is to face the ostium of the branching vessel. One technique for precisely locating the stent is by initially introducing two guidewires into the main vessel, one guidewire extending through the bifurcation into one branch vessel, and the other guidewire extending through the bifurcation into the other branch vessel, and then using the two guidewires for guiding the stent, which is mounted on a delivery device, e.g., a balloon angioplasty catheter, to its precise longitudinal position and radial orientation before deploying the stent. One such technique involving the initial placement of two guidewires is described, for example, in U.S. Pat. No. 5,749,825 to Fischell et al.

However, in such a two-wire technique, due to the tortuosity of the vascular system, the physician must torque the delivery system in order to deliver the guidewires to their correct location. Because of this torquing, the two guidewires frequently tend to cross over one another and/or entangle during their use for guiding the stent delivery device. Such an entanglement or crossover, if it should occur, may result in an inability of the device to be delivered by the physician, requiring the procedure to be started anew.

There is thus a widely recognized need for, and it would be highly advantageous to have, a method for delivering stents to bifurcations devoid of the above limitations.

SUMMARY OF THE INVENTION

An object of the present invention is to provide a method of deploying a stent in a vessel bifurcation which method substantially reduces or eliminates the possibility of wire entanglement or cross-over when deploying the stent.

The invention is particularly useful in deploying stents in coronary blood vessel bifurcations, and is therefore described below with respect to such applications. It will be appreciated, however, that the invention could also be used for deploying stents in other vessel bifurcations such as peripheral blood vessels, or vessels related to the renal, gastrointestinal and reproductive systems or any other system in the body wherein a main vessel is split into two (or more) branch vessels.

According to one aspect of the present invention, there is provided a method of introducing a first and second vessel guidewire into two branches of a vessel, the method including inserting a first guidewire into a first vessel, inserting a second guidewire into said first vessel, advancing a delivery system through the first vessel over the first guidewire and the second guidewire, the delivery system having a first lumen that slidably engages the first guidewire and a second lumen alongside the first lumen that slidably engages the second guidewire, positioning the delivery system in a region of a bifurcation, retracting the second guidewire proximally until a distal end of the second guidewire is in a region of a bifurcation, and advancing the second guidewire through the second lumen into the second vessel.

According to a further aspect of the present invention, there is provided a method of deploying a stent in a bifurcation of a main vessel which separates into first and second branch vessels, the stent including a proximal end to be deployed in the main vessel on the proximal side of the bifurcation, and a distal end to be deployed in the first branch vessel on the distal side of the bifurcation. The method includes introducing the distal end of a first guidewire through the main vessel and the bifurcation into the first branch vessel, introducing the distal end of a second guidewire through the main vessel and the bifurcation into the first branch vessel, providing a stent delivery device including a main lumen for receiving the guidewire, a branch lumen, and an expandable stent, inserting the proximal end of the first guidewire into the distal end of the main lumen of the stent delivery device, inserting the proximal end of the second guidewire into the distal end of the main lumen of the stent delivery device, guiding the stent delivery device along the first guidewire through the main vessel and along the second guidewire through the branch vessel to an initial position adjacent to the proximal side of the bifurcation, retracting the second guidewire, advancing the second guidewire into the second branch vessel, advancing the stent delivery device, while tracked by the first guidewire in the first branch vessel and by the second guidewire in the second branch vessel, to the predetermined deployment position with respect to the bifurcation, to bring the distal end of the stent into the first branch vessel, while the proximal end of the stent still remains in the main vessel, radially expanding the stent, and removing the stent delivery device.

According to another aspect of the present invention, there is provided a method of introducing two guidewires into a first and a second vessel, the method including inserting a first guidewire into the first vessel, advancing a delivery system through the first vessel over the first guidewire, the delivery system having a first lumen that slidably engages the first guidewire and a second lumen alongside the first lumen, positioning the delivery system in a region of a bifurcation, and advancing a second guidewire through the second lumen into the second vessel.

According to yet another aspect of the present invention, there is provided a method of advancing a delivery system at a bifurcation, the method including advancing a delivery system over a first guidewire, the delivery system having a first lumen for insertion of the first guidewire and a second lumen for insertion of a second guidewire, wherein the first lumen and the second lumen are separated by a barrier and wherein the advancing is done by positioning a first guidewire within the first lumen, and thereafter introducing a second guidewire through the second lumen and into a second vessel.

According to a further aspect of the present invention, there is provided a method of deploying a stent in a bifurcation of a main vessel which separates into first and second branch vessels, the stent including a proximal end to be deployed in the main vessel on the proximal side of the bifurcation, and a distal end to be deployed in the first branch vessel on the distal side of the bifurcation. The method includes introducing the distal end of a first guidewire through the main vessel and the bifurcation into the first branch vessel, providing a stent delivery device including a main lumen for receiving the guidewire, a branch lumen, and an expandable stent, inserting the proximal end of the first guidewire into the distal end of the main lumen of the stent delivery device, guiding the stent delivery device along the first guidewire through the main vessel to an initial position adjacent to the proximal side of the bifurcation, moving a second guidewire through the branch lumen of the stent delivery device, advancing the second guidewire into the second branch vessel, advancing the stent delivery device, while tracked by the first guidewire in the first branch vessel, and by the second guidewire, in the second branch vessel, to the predetermined deployment position with respect to the bifurcation, to bring the distal end of the stent into the first branch vessel, while the proximal end of the stent still remains in the main vessel, radially expanding the stent, and removing the stent delivery device, Either of the first and second guidewire may be pre-loaded in the first or second lumen, respectively. Alternatively, the first or the second guidewire may be introduced after the delivery device is advanced in the vessel.

According to further embodiments, the vessels are blood vessels, the first vessel is either a main vessel or a branch vessel and the second vessel is either a main vessel or a branch vessel.

According to further embodiments, the delivery system is a catheter with a stent. The stent has an optional side hole for placing one of the guidewires through so as to enter a branch vessel. The side hole may be the same or different than other openings in the wall of the stent. The stent is either self-expandable, or expandable by an inflatable balloon.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples arc illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a method for deploying a stent at or near a bifurcation. Specifically, the method of the present invention allows insertion of two wires into two branches of a vessel while avoiding wire entanglement.

Figure 1A:
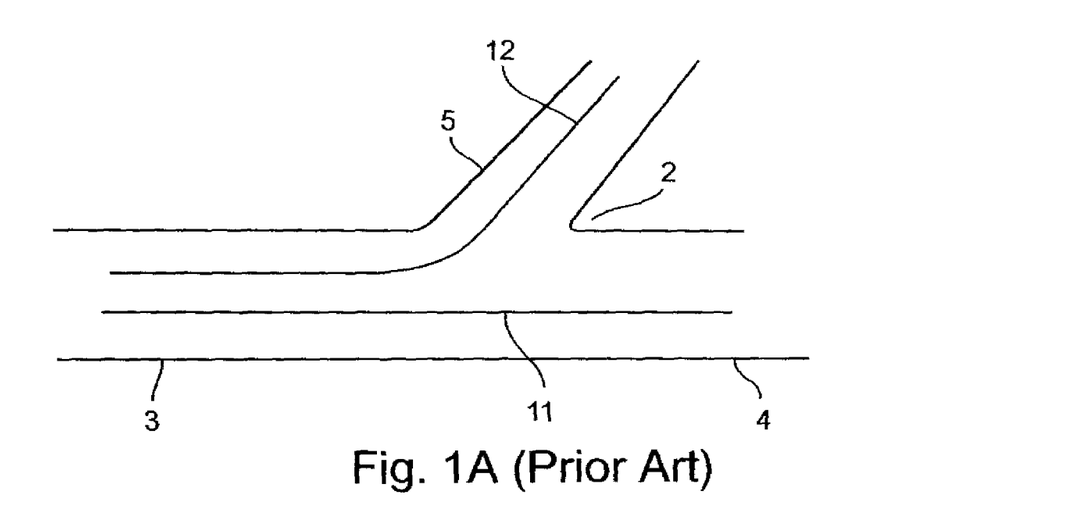
FIGS. 1A-1B illustrate a two-wire technique, as, known in the prior art, for deploying a stent in an arterial bifurcation.
Figure 1B:
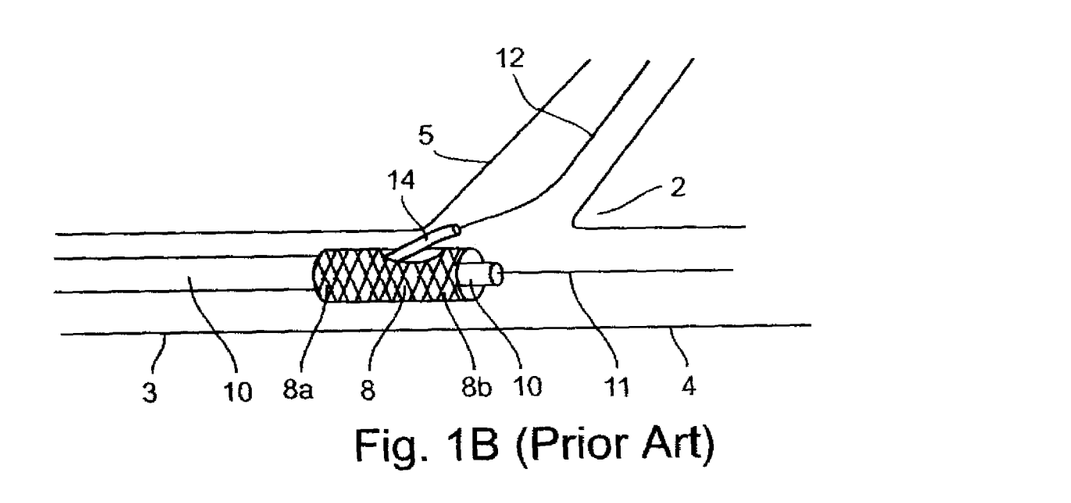

For purposes of better understanding the present invention, as illustrated in FIGS. 2-5 of the drawings, reference is first made to the two-wire method of deploying a stent in a vessel bifurcation (i.e. the prior art) as illustrated in FIGS. 1A and 1B. In the example illustrated in FIGS. 1A and 1B, the bifurcation, generally designated 2, involves a main vessel 3, which splits into a main vessel continuation 4, and a branch vessel 5. The point at which the two branches 4, 5 intersect is commonly called the "saddle point" of the bifurcation.

The stent to be deployed is generally designated 8. It includes a proximal end 8A to be deployed in the main vessel 3, and a distal end 8B to be deployed in the main vessel continuation 4. For this purpose, it is delivered by a stent delivery device, generally designated 10, to its precise longitudinal position and radial orientation before it is so deployed. The stent delivery device 10 illustrated in FIG. 1B is a balloon angioplasty catheter, and the stent 8 is outwardly expandable, so that when the stent is precisely positioned within the bifurcation 2, the inflation of the balloon of the stent delivery device 10 expands the stent to press its proximal end 8a firmly against the wall of the main vessel 3, and its distal end 8b firmly against the wall of the main vessel continuation 4.

The prior art technique illustrated in FIGS. 1A and 1B for precisely locating the stent 8 before its deployment is a two-wire technique. According to this technique, a main guidewire 11 is initially passed through the main vessel 3, through the bifurcation 2, and into the main vessel continuation 4, and a branch guidewire 12 is also initially passed through the main vessel 3, the bifurcation 2, and into the branch 5, as depicted in FIG. 1A. The main guidewire 11 and the branch guidewire 12, after being so placed, are then used for tracking the stent delivery device 10 to its proper position before deploying the stent 8, as depicted in FIG. 1B.

As briefly described above, a serious problem with the two-wire technique illustrated in FIG. 1 is the risk of entanglement or crossover of the two guidewires 11, 12, during the movement of the stent delivery device 10 along these guidewires toward the bifurcation 2. If such an entanglement or crossing of the guidewires should occur, this would generally result in the cardiologist having to pull back the wires and possibly the stent delivery device in order to re-commence the procedure. In doing this, the cardiologist may dislodge the stent or dissect or even puncture the vessel.

Figure 2A:
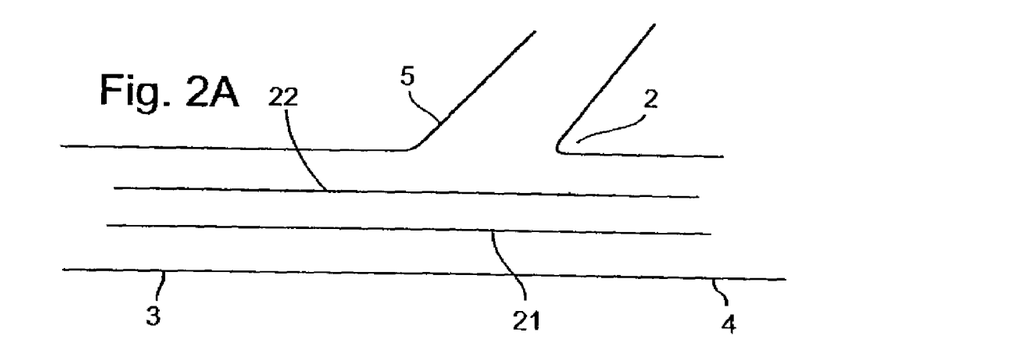
FIGS. 2A-2G are diagrammatical views illustrating the steps of deploying a stent in a bifurcation in accordance with a preferred embodiment of the present invention.
Figure 2B:
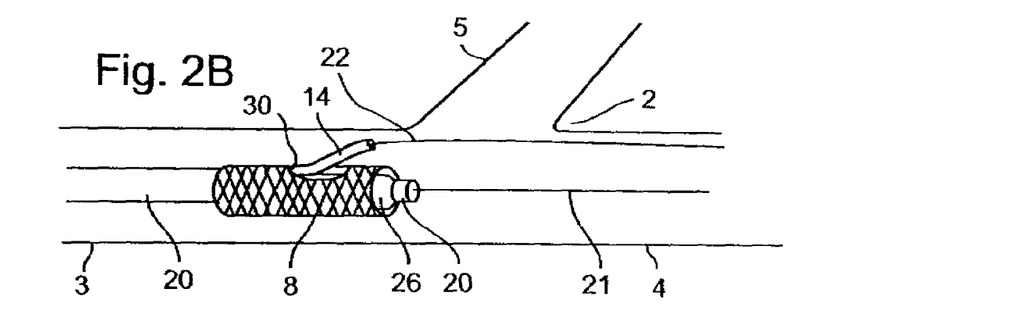
Figure 2C:
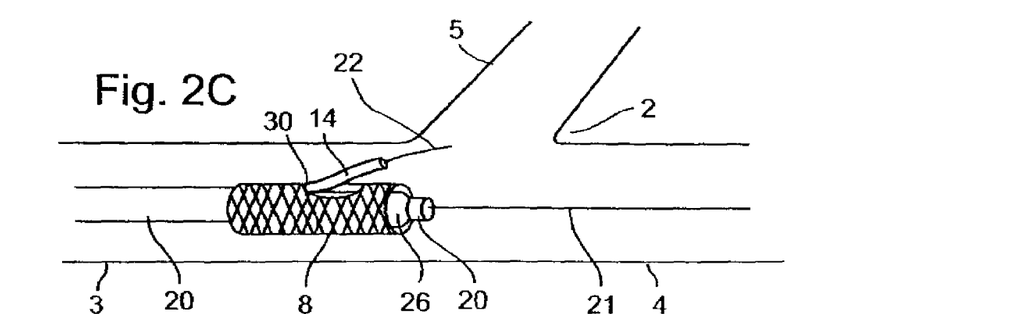
Figure 2D:
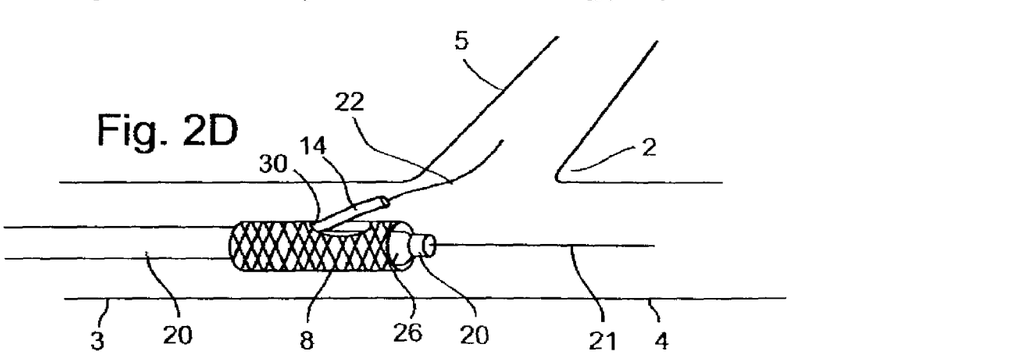
Figure 2E:
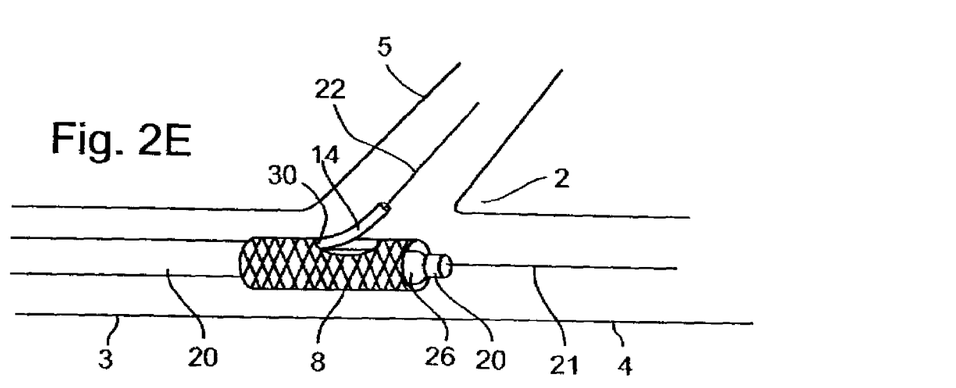
Figure 2F:
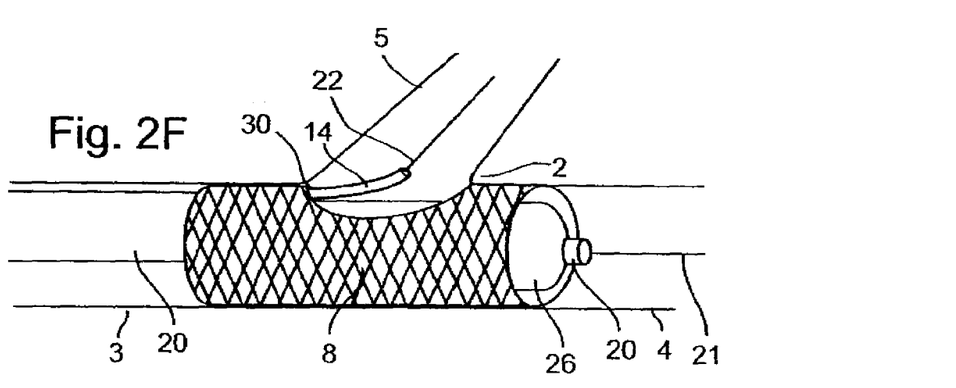
Figure 2G:
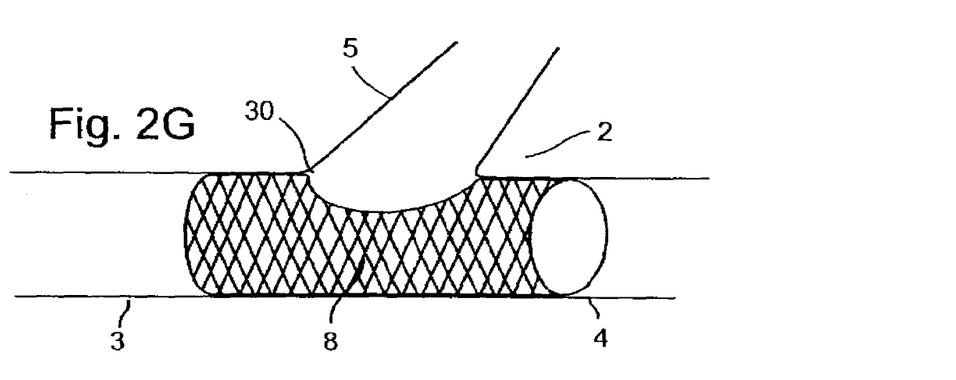

Reference is now made to FIGS. 2A-2G, depicting a method of deploying a stent according to a preferred embodiment of the present invention. FIGS. 2B-2F illustrate a stent delivery device, generally designated 20, to be deployed in a bifurcation corresponding to bifurcation 2 shown in FIG. 1, namely one including a main vessel 3 split into a main vessel continuation 4 and a branch vessel 5. As shown in FIG. 2A, both a main guidewire 21 and a branch guidewire 22 arc initially placed in the main vessel 3, preferably extending into main vessel continuation 4. As shown in FIG. 2B, delivery system 20 is then advanced over both guidewires, with main guidewire 21 being positioned through a main lumen of delivery device 20 and with branch guidewire 22 being positioned through a branch lumen of delivery device 20, the construction of which will be described in further detail hereinbelow. As shown in FIG. 2C, branch guidewire 22 is then retracted until its tip is opposite or proximal to the ostium of the branch vessel 5. Subsequently, as shown in FIG. 2D, branch guidewire 22 is advanced into the branch vessel 5. Next as shown in FIG. 2E, delivery device 20 is advanced over both wires until the stent is in its optimal position with respect to the ostium of the bifurcation. The stent is then deployed, as shown in FIG. 2F. Finally, delivery device 20 and guidewires 21 and 22 are removed, leaving only the expanded stent 8 in place.

In an alternative embodiment, both guidewires 21, 22 are initially placed in the branch vessel 5, and delivery system 20 is advanced over the two wires. In the alternative embodiment just described, main guidewire 21 is retracted and subsequently advanced through main vessel 3 and into main vessel continuation 4. It is essential that guidewires 21 and 22 are both located in the same vessel, whether that vessel is the main vessel 3, main vessel continuation 4, or branch vessel 5. In this way, crossover and entanglement of the wires is minimized.

The method described above is particularly useful for rapid exchange systems, such as those disclosed in U.S. Provisional Patent Application Ser. No. 60/413,552, filed on Sep. 26, 2002 and incorporated by reference herein in its entirety, and described further hereinbelow, and any other rapid exchange system used in stent delivery. The method may also be used for any other delivery system, including over-the wire systems which are well known in the art, as well as systems such as the ones disclosed in pending U.S. patent application Ser. No. 09/455,299, filed Dec. 6, 1999; Ser. No. 09/1741,761, filed Dec. 18, 2000; and Ser. No. 09/663,111 filed Sep. 15, 2000, all of which are incorporated herein by reference in their entireties and described finer hereinbelow. Furthermore, this method may be useful for a dual stent system, in which a main stent and a side branch stent, or two portions of one stent, are used in the bifurcation. This type of stent may be useful, for example, for drug delivery into a bifurcated vessel.

Reference is now made to FIGS. 3A-3F, which illustrate an alternative embodiment of the present invention. FIGS. 3B-3F illustrate a stent delivery device, generally designated 20, to be deployed in a bifurcation corresponding to bifurcation 2 shown in FIG. 1, namely one including a main vessel 3 split into a main vessel continuation 4 and a branch vessel 5. In the technique illustrated in FIGS. 3A-3F, a single guidewire is used to track the delivery device 20. It should be noted that an additional wire may be placed in the blood vessel prior to the procedure described, and that the physician can utilize this additional wire for any one or more of the procedures which precede stent placement, such as, but not limited to, fluoroscope visualization, stentless balloon angioplasty or predilatation, insertion of a visualization catheter, use with additional diagnostic and/or therapeutic devices, etc. However, the additional wire plays no role in the delivery of the device and as such, will generally not be included in the description to follow.

Figure 3A:
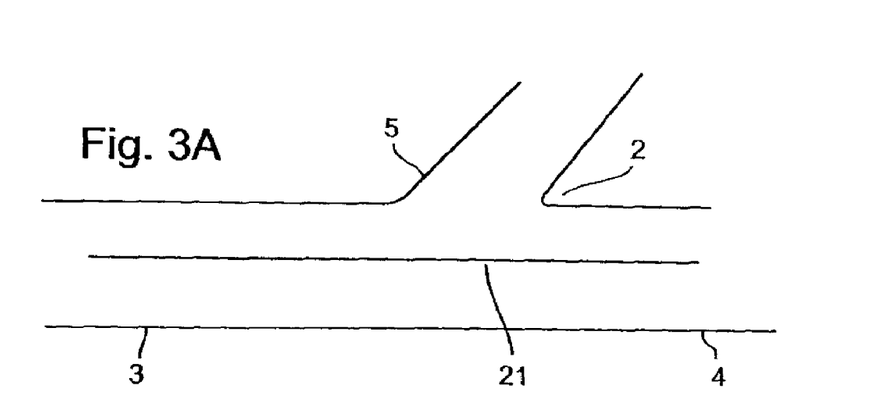
FIGS. 3A-3F are diagrammatical views illustrating the steps of deploying a stent in a bifurcation in accordance with another preferred embodiment of the present invention.
Figure 3B:
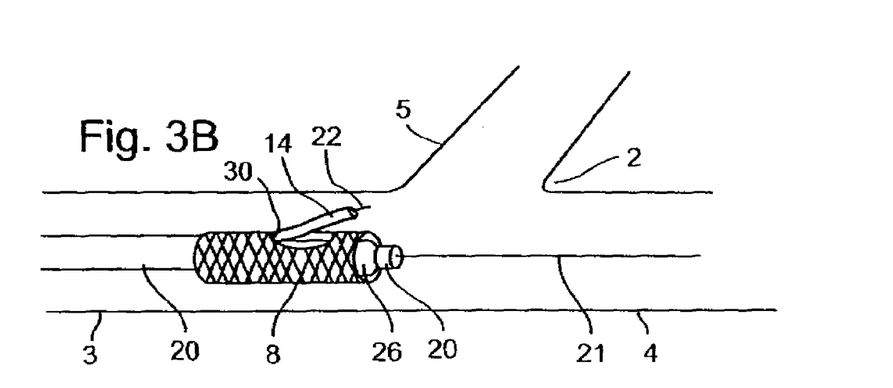

As shown in FIG. 3A, a main guidewire 21 is initially placed through the main vessel 3, the bifurcation 2, and the main vessel continuation 4. As shown in FIG. 3B, delivery device 20 having a stent 8 thereon is applied to the guidewire 21, by passing the guidewire 21 through main lumen 12, and moving the delivery device 20 to its initial position, a preferred embodiment of which is illustrated in FIG. 3B. In this initial position, the delivery device 20 is located proximal to the proximal end of the bifurcation 2. In alternative embodiments, delivery device 20 may be initially placed directly opposite or distal to the bifurcation 2, and then adjusted accordingly. If stent 8 is formed with a side opening 30, the construction of which will be described further hereinbelow, the stent delivery device may be rotated, so as to radially position the stent properly, e.g., with the side opening facing the ostium of the branch vessel. However, it should be noted that automatic alignment of the side opening may take place once the branch guidewire 22 is inserted into the branch vessel 5 and the delivery device 20 is advanced.

In one embodiment of the invention, the branch guidewire 22 may be pre-loaded in a branch lumen 14 of the delivery device 20, with the distal end of branch guidewire 22 protruding from a side of the stent, preferably from a designated side hole 30, so that the branch guidewire 22 is moved with the delivery device 20 to the initial position, a preferred embodiment of which is illustrated in FIG. 3B. In this embodiment, the distal end of branch lumen 14 may also protrude from the side of the delivery device 20 and the stent 8 carried thereby. In the latter case, branch guidewire 22 might not protrude from the side of the stent, as it can be advanced to protrude therefrom at a later stage.

In an alternative embodiment the branch guidewire 22 would be inserted into branch lumen 14 of the delivery device 20 only after the delivery device 20 has been moved to its initial position. In both embodiments, the distal end of branch guidewire 22 could protrude through side opening 30 in the stent, or through one of the cellular or spiral spaces in the stent or any other opening, if no side opening is present.

Figure 3C:
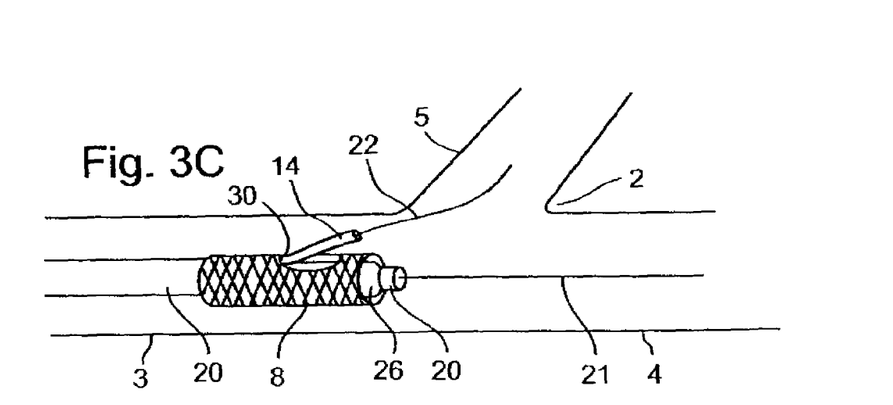

In either case, when the delivery device 20 has been moved to the vicinity of its initial position, the branch guidewire 22 is manipulated from its proximal end so that its distal end is advanced into the branch vessel 5, as shown in FIG. 3C.

Figure 3D:
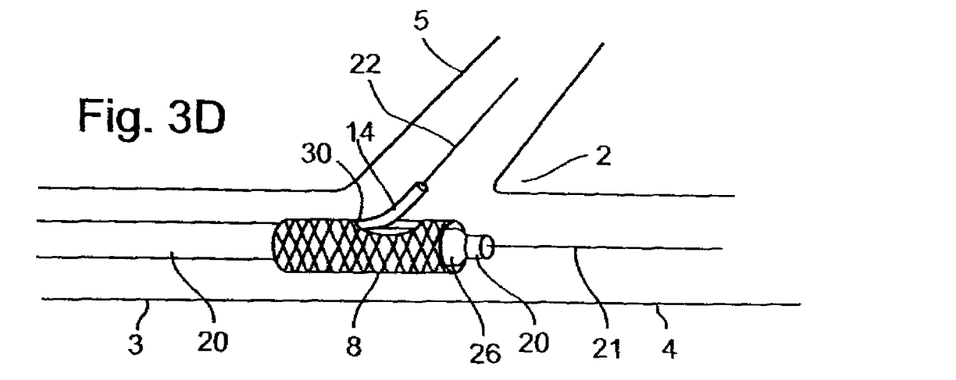
Figure 3E:
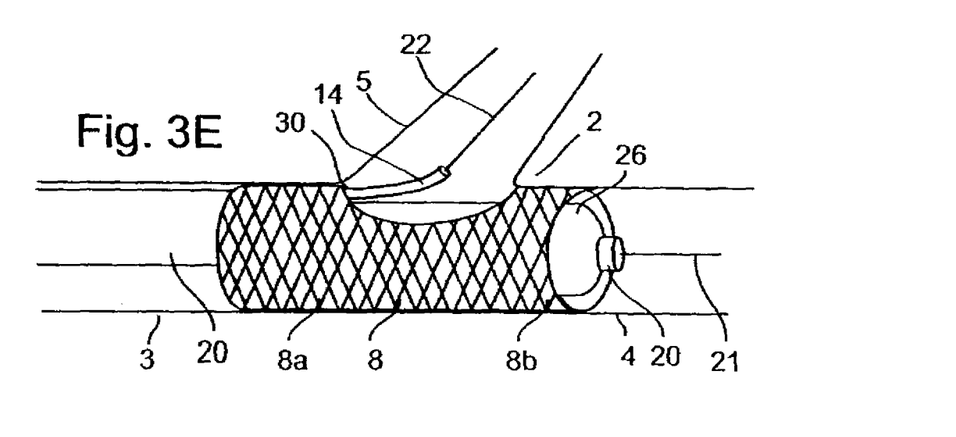
Figure 3F:
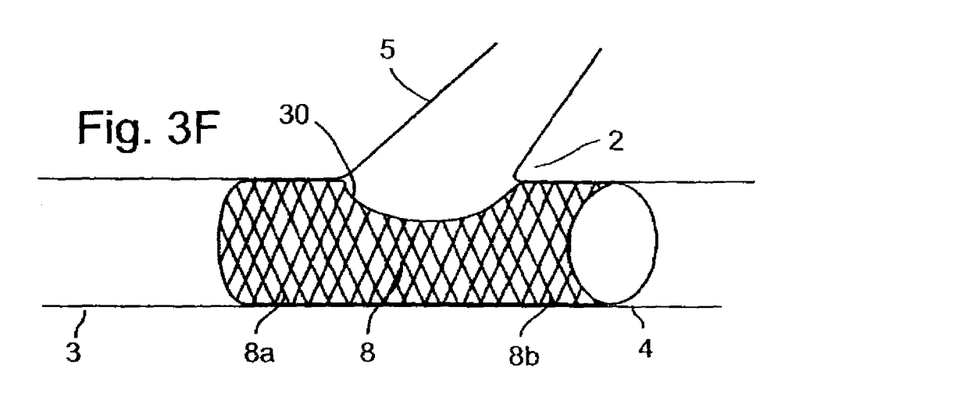

The delivery device 20 is then further advanced or retracted as the case may be, to its final, stent-deployment position, a preferred embodiment of which is shown in FIG. 3D. The preferred stent-deployment position of the sent delivery device 20 is the location where the intersection of the branch guidewire 22 with the balloon 26 (commonly called the "crotch point") generally coincides with the saddle point of the main vessel continuation 4 and branch vessel 5, as described, for example, in U.S. Pat. No. 5,749,825.

FIG. 3D illustrates a preferred embodiment of the final stent-deployment position of the delivery device 20, wherein the delivery device 20 locates the stent 8 both longitudinally and radially with respect to the bifurcation 2, after it is tacked over the main guidewire 21 in the main vessel continuation 4.

Figure 4:
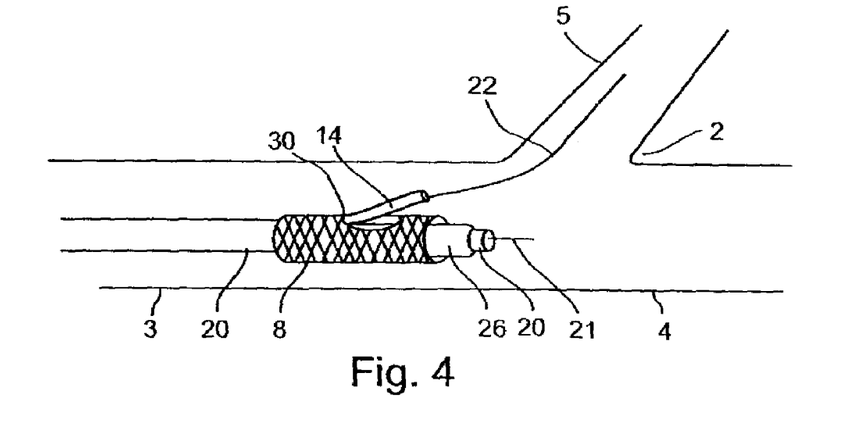
FIG. 4 illustrates a stent deploying device for deploying a stent in a bifurcation in accordance with another embodiment of the method of the present invention.

In an alternative embodiment, shown in FIG. 4, the branch guidewire 22 is used to track the delivery device 20. As shown in FIG. 4, branch guidewire 22 is initially placed through the main vessel 3, the bifurcation 2, and the branch vessel 5. For precisely locating the delivery device 20 with respect to both its longitudinal position and its radial orientation, a main guidewire 21 is used. That is, the main guidewire 21 is not initially placed into the bifurcation 2 as in the prior art described above with respect to FIG. 1, but rather is loaded into the delivery device 20 before or after the delivery device 20 is advanced over the branch guidewire 22, to an initial position, and in this alternative embodiment the main guidewire 21 is then advanced through the delivery device 20, through the stent 8 into the main vessel continuation 4. The delivery device 20 is then tracked over the main guidewire 21 in the main vessel continuation 4, and by the branch guidewire 22 in the branch vessel 5, to its final longitudinal and radial position before the stent 8 carried thereon is deployed with respect to the main vessel 3 and the main vessel continuation 4.

It will also be appreciated that if the bifurcation 2 has already received an additional guidewire then this additional guidewire, which is not utilized in the stent positioning methods described herein, is to be removed prior to inflation of the balloon 26. If the additional guidewire 66 is not so removed, it will be trapped between the expanded stent 8 and the vessel wall. The main guidewire and/or the branch guidewire will typically be last to be removed from the patient vascular system.

It should be noted that in this preferred embodiment the branch guidewire 22 is not initially placed into the bifurcation 2 as in the prior art described above with respect to FIG. 1A, but rather is carried by, or received by, the delivery device 20 before or after the delivery device bas been moved, over the main guidewire, to an initial position near the bifurcation, so that it does not become entangled with or cross over the main guidewire 21 during the positioning of the delivery device 20.

In an alternative embodiment, shown in FIG. 4, the branch guidewire 22 is used to track the delivery device 20. As shown in. FIG. 4, branch guidewire 22 is initially placed through the main vessel 3, the bifurcation 2, and the branch vessel 5. For precisely locating the delivery device 20 with respect to both its longitudinal position and its radial orientation, a main guidewire 21 is used. That is, the main guidewire 21 is not initially placed into the bifurcation 2 as in the prior art described above with respect to FIG. 1, but rather is loaded into the delivery device 20 before or after the delivery device 20 is advanced over the branch guidewire 22, to an initial position, and in this alternative embodiment the main guidewire 21 is then advanced through the delivery device 20, through the stent 8 into the main vessel continuation 4. The delivery device 20 is then tracked over the main guidewire 21 in the main vessel continuation 4, and by the branch guidewire 22 in the branch vessel 5, to its final longitudinal and radial position before the stent 8 carried thereon is deployed with respect to the main vessel 3 and the main vessel continuation 4.

The delivery device 20 may be of a similar construction as that disclosed in pending U.S. patent application Ser. No. 09/455,299, filed Dec. 6, 1999; Ser. No. 09/741,761, filed Dec. 18, 2000; and Ser. No. 09/663,111 filed Sep. 15, 2000, all of which are incorporated herein by reference in their entireties. In other embodiments, the delivery device 20 may be of a similar construction as other dual lumen delivery devices, such as the one disclosed in U.S. Pat. No. 5,749,825 to Fischell et al.

Figure 5:
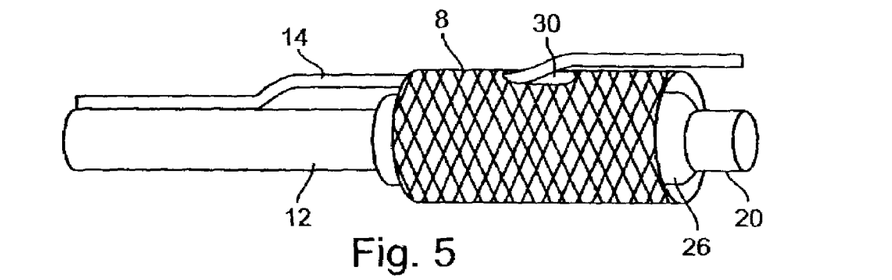
FIG. 5 is an enlarged view of the stein delivery device illustrated in FIGS. 2-4.

Briefly, as shown in FIG. 5, a delivery device 20 may be a catheter with a catheter body 12 and a side member 14 that is adjacent to catheter body 12. Side member 14 may be slidably movable with respect to catheter body 12 or may be attached thereto. In one embodiment, catheter body 12 has a balloon 26 around which a stent 8 is crimped. In another embodiment, stent 8 is self-expandable and balloon 26 is not included. In a preferred embodiment, stent 8 has a side hole 30 for alignment with an ostium of a branch vessel. Various types of side hole are described in U.S. Provisional Patent Application No. 60/404,756, filed Aug. 21, 2002, incorporated herein by reference in its entirely. Side hole 30 may be of various shapes and sizes, and may also have a portion designed to partially extend into the branch vessel.

Figure 6:
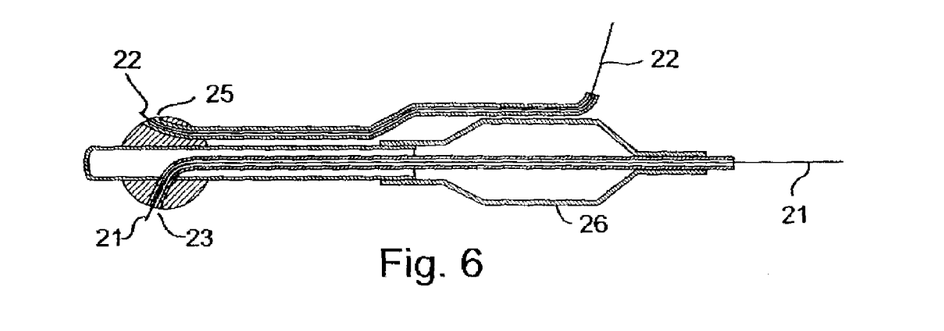
FIG. 6 is a cross sectional view of a stent delivery device used for deploying a stent in accordance with another embodiment of the method of the present invention.
Figure 7:
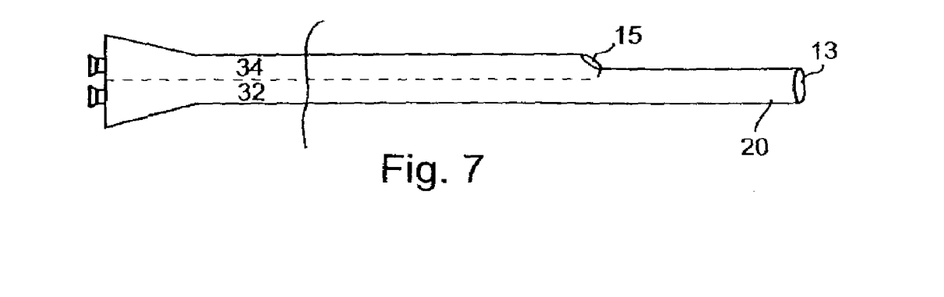
FIG. 7 illustrates a delivery device for delivering two wires to a bifurcation, in accordance with an embodiment of the method of the present invention.

In an alternative embodiment of the present invention, a rapid exchange delivery system is used, such as the one described in U.S. Provisional Patent Application Ser. No. 60/413,552, filed on Sep. 26, 2002 and incorporated by reference herein in its entirety. A system such as the one described is shown in FIG. 6. The system disclosed in the above-referenced patent application and shown in FIG. 6 is a rapid exchange system with a dual lumen catheter, specifically designed for vessel bifurcations.

As shown in FIG. 6, delivery device 20 has exit ports 23 and 25 for the main guidewire 21 and branch guidewire 22, respectively, which exit ports are located at a distance of approximately 1 to 150 cm from the distal end of delivery device 20. In a preferred embodiment, the exit ports 23 and 25 are located at a distance of approximately 10 to 20 cm from the distal end of delivery device 20. In an exemplary preferred embodiment, the exit ports 23 and 25 are located at a distance of 15 cm from the distal end of delivery device 20. In this system, a three-way bond is created at exit ports 23 and 25, maintaining three lumens: exit ports 23 and 25, and a lumen for fluid infusion for inflation of balloon 26.

In alternative embodiments, delivery device 20 is used for delivering guidewires 21 and 22 to a main vessel continuation 4 and a branch vessel 5, without having a stent placed on the delivery device 20. An example of such a delivery device includes a catheter with a two-headed balloon or a dual lumen balloon. In this embodiment, delivery device 20 may be of a similar construction as that disclosed in pending U.S. patent application Ser. No. 09/816,690, filed Mar. 22, 2001, and incorporated by reference in its entirety.

Briefly, delivery device 20 has two lumens 32 and 34 passing therethrough. As can be seen in FIG. 6, lumen 32 has a distal end opening 13 which is preferably disposed at or near the end of the delivery device. Lumen 34 has a distal end opening 15 which is preferably disposed at a location some distance proximal to the distal end of the delivery device 20. Main branch guidewire 21 (not shown) is receivable through lumen 32 and branch guidewire 22 (not shown) is receivable through lumen 34.

While the invention has been described with respect to two preferred embodiments, it will be appreciated that these are set forth merely for purposes of example, and that many other variations, modifications and applications or the invention may be made. It should be readily apparent that either the two-wire method illustrated in FIGS. 2A-2G, or the one wire method illustrated in FIGS. 3A-3F may be used for introducing the wires of any of the delivery devices described herein, or any other delivery device in which two wires are needed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of deploying a stent in a bifurcation of a main vessel which separates into first and second branch vessels, the method comprising:
   first, inserting a first guidewire into the main vessel such that the first guidewire extends across the bifurcation and into the first branch vessel;
   providing a stent delivery device including a main lumen for receiving the first guidewire, a branch lumen for receiving a second guidewire, and an expandable stent disposed thereon;
   after inserting the first guidewire into the main vessel, inserting the second guidewire into the branch lumen of the stent delivery device such that a distal end of the second guidewire is adjacent to a distal end of the branch lumen;
   after the second guidewire is inserted into the branch lumen, advancing the stent delivery device over the first guidewire through the main vessel to a position adjacent to the bifurcation;
   without retracting the second guidewire, advancing the second guidewire through the distal end of the branch lumen and into the second branch vessel;
   advancing the stent delivery device over the first guidewire and the second guidewire to a stent deployment position adjacent the bifurcation; and
   radially expanding the stent with at least a proximal end of the stent extending into the main vessel.

2. The method of claim 1, wherein a distal end of said stent extends into the first branch vessel in the stent deployment position.

3. The method of claim 1, further comprising:
   removing the stent delivery device.

4. The method of claim 3, wherein the stent delivery device further comprises an inflatable balloon around which the stent is positioned, and wherein the step of radially expanding the stent comprises inflating the balloon to radially expand the stent.

5. The method of claim 4, wherein the radial expansion of a proximal end and a distal end of the stent are done separately.

6. The method of claim 5, further comprising:
   deflating the balloon; and
   removing the balloon together with the stent delivery device.

7. A method of deploying a stent in a bifurcation of a main vessel which separates into first and second branch vessels, the method comprising:
   first, inserting a first guidewire into the main vessel such that the first guidewire extends across the bifurcation and into the first branch vessel;
   providing a stent delivery device including a branch lumen for receiving the first guidewire, a main lumen for receiving a second guidewire, and an expandable stent disposed thereon, wherein the main lumen extends to a distal end of the stent delivery device;
   after inserting the first guidewire into the main vessel, inserting the second guidewire into the main lumen of the stent delivery device such that a distal end of the second guidewire is adjacent to a distal end of the main lumen;
   after the second guidewire is inserted into the main lumen, advancing the stent delivery device over the first guidewire through the main vessel to a position adjacent to the bifurcation; and
   without retracting the second guidewire, advancing the second guidewire through the distal end of the main lumen and into the second branch vessel.

8. The method of claim 7 further comprising advancing the stent delivery device over the first guidewire and the second guidewire to a stent deployment position adjacent to the bifurcation.

9. The method of claim 8 wherein a distal end of said stent extends into the first branch vessel and a proximal end of the stent extends into the main vessel in the stent deployment position.

10. The method of claim 8 further comprising:
    radially expanding the stent; and
    removing the stent delivery device.

11. The method of claim 10, wherein the stent delivery device further comprises an inflatable balloon around which the stent is positioned, and wherein the step of radially expanding the stent comprises inflating the balloon to radially expand the stent.

12. The method of claim 11, wherein the radial expansion of a proximal end and a distal end of the stent are done separately.

13. The method of claim 12, further comprising:
    deflating the balloon; and
    removing the balloon together with the stent delivery device.

14. A method of deploying a stent in a bifurcation of a main vessel which separates into first and second branch vessels, the method comprising:
    first, inserting a first guidewire into the main vessel such that the first guidewire extends across the bifurcation and into one of the first branch vessel or the second branch vessel;
    providing a stent delivery device including a main guidewire lumen, a branch guidewire lumen, and an expandable stent disposed thereon, wherein the main guidewire lumen extends to a distal end of the stent delivery device;
    after inserting a first guidewire into the main vessel, inserting a second guidewire into either the main guidewire lumen or the branch guidewire lumen of the stent delivery device such that a distal end of the second guidewire is adjacent to a distal end of the respective lumen;
    after the second guidewire is inserted into either the main guidewire lumen or the branch guidewire lumen, advancing the stent delivery device over the first guidewire through the main vessel to a position adjacent to the bifurcation;
    without retracting the first guidewire or the second guidewire, advancing the second guidewire through the distal end of either the main guidewire lumen or the branch guidewire lumen and into the second branch vessel;
    advancing the stent delivery device over the first guidewire and the second guidewire to a stent deployment position adjacent the bifurcation; and
    radially expanding the stent with at least a proximal end of the stent extending into the main vessel.

15. The method of claim 1, wherein the second guidewire is not initially placed into the bifurcation, but is carried by the stent delivery device to the bifurcation during the step of advancing the stent delivery device over the first guidewire.

16. The method of claim 7, wherein the second guidewire is not initially placed into the bifurcation, but is carried by the stent delivery device to the bifurcation during the step of advancing the stent delivery device over the first guidewire.

17. The method of claim 14, wherein the second guidewire is not initially placed into the bifurcation, but is carried by the stent delivery device to the bifurcation during the step of advancing the stent delivery device over the first guidewire.

\* \* \* \* \*